United States Patent [19]
Witkowski

[11] Patent Number: 4,497,814
[45] Date of Patent: Feb. 5, 1985

[54] 2-(PYRIDINYL)-1,2,4-TRIAZOLO[1,5-A]PYRIMIDINES AND DERIVATIVES USEFUL IN INCREASING CARDIAC CONTRACTILITY

[75] Inventor: Joseph T. Witkowski, Morris Township, Morris County, N.J.

[73] Assignee: Schering Corporation, Kenilworth, N.J.

[21] Appl. No.: 408,359

[22] Filed: Aug. 16, 1982

[51] Int. Cl.³ .................. A61K 31/505; C07D 487/04
[52] U.S. Cl. ..................................... 514/258; 544/263
[58] Field of Search ....................... 544/263; 546/276; 424/251

[56] References Cited

U.S. PATENT DOCUMENTS

| | | | |
|---|---|---|---|
| 2,444,605 | 7/1948 | Heimbach et al. | 544/263 |
| 2,852,375 | 9/1958 | Tinker | 544/263 |
| 3,663,527 | 5/1972 | Hegar | 546/276 |
| 3,689,488 | 9/1972 | Dukes | 544/263 |

Primary Examiner—Paul M. Coughlan, Jr.
Attorney, Agent, or Firm—Gerald S. Rosen; Bruce M. Eisen

[57] ABSTRACT

Disclosed are 2-(pyridinyl)-1,2,4-triazolo[1,5-a]pyrimidines and derivatives which are effective in increasing cardiac contractility. These compounds are useful in the treatment of congestive heart failure preferably by oral or parenteral administration.

26 Claims, No Drawings

2-(PYRIDINYL)-1,2,4-TRIAZOLO[1,5-A]PYRIMIDINES AND DERIVATIVES USEFUL IN INCREASING CARDIAC CONTRACTILITY

SUMMARY OF THE INVENTION

This invention relates to certain 2-(pyridinyl)-1,2,4-triazolo-[1,5-a]pyrimidines and derivatives which are useful in increasing cardiac contractility, to pharmaceutical compositions containing such compounds, to a method of treating a patient by administering an effective amount of such compounds to increase cardiac contractility in said patient and to novel intermediates useful in the synthesis of 2-(pyridinyl)-1,2,4-triazolo[1,5-a]pyrimidines.

The compounds of the present invention are selected from the group consisting of

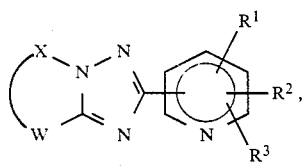
A

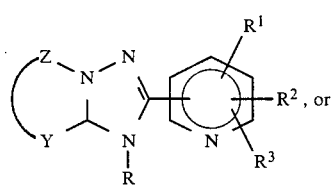
B

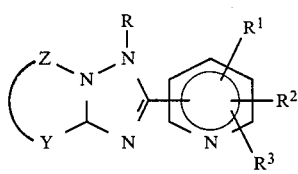
C wherein

W and X together with the carbon and nitrogen of the triazolo ring are joined to form a heterocyclic ring selected from the group consisting of

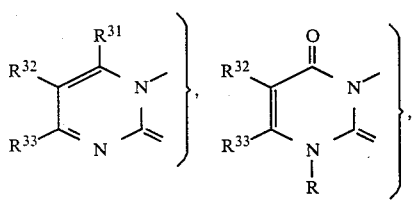

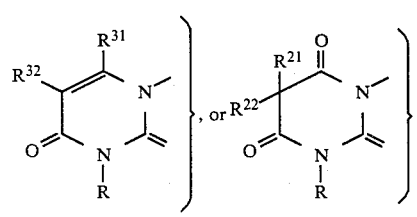

Y and Z together with the carbon and nitrogen of the triazolo ring are joined to form a heterocyclic ring selected from the group consisting of

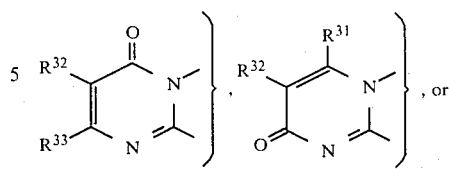

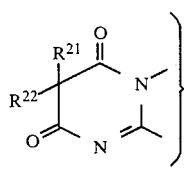

R is hydrogen, lower alkyl or lower aralkyl; $R^1$, $R^2$ and $R^3$ are independently selected from hydrogen, hydroxy, halogen, lower alkoxy, lower alkyl and amino;

$R^{31}$, $R^{32}$ and $R^{33}$ are independently selected from hydrogen, lower alkyl, hydroxy, cyano, $-NR^4R^5$ wherein $R^4$ is hydrogen, lower alkyl, or

wherein $R^6$ is lower alkyl, and $R^5$ is hydrogen, lower alkyl, or together with $R^4$ is joined to form a ring containing 4 to 6 carbon atoms,

wherein $R^7$ is hydroxy, lower alkoxy, or $-NR^8R^9$ wherein $R^8$ and $R^9$ are independently selected from hydrogen or lower alkyl;

wherein M is sulfur or NH;

$R^{21}$ and $R^{22}$ are independently selected from hydrogen or lower alkyl;

with the proviso excluding 7-hydroxy-5-lower alkyl-2-(4'-pyridinyl)-1,2,4-triazolo[1,5-a]pyrimidines;

and the pharmaceutically acceptable salts thereof.

This invention is also related to novel intermediates which are useful in the synthesis of 2-(pyridinyl)-1,2,4-triazolo[1,5-a]pyrimidines. These compounds are selected from the group consisting of

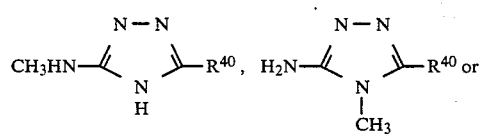

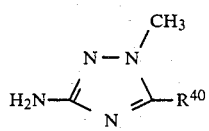

wherein R[40] is pyridinyl or pyridinyl substituted with 1 to 3 substituents independently selected from halogen, lower alkyl, hydroxy, lower alkoxy and amino.

Unless otherwise stated, the term "alkyl" includes both branched- and straight-chain alkyl groups. The term "lower alkyl" includes alkyl groups of from 1 to 6 carbons and includes for instance methyl, ethyl, n-propyl, isopropyl, t-butyl, n-hexyl and the like.

The term "lower aralkyl" refers to lower alkyl groups substituted by an aryl group and includes, for instance, benzyl, phenethyl and the like. Typical aryl groups include, for instance, phenyl, napthyl and the like.

The term "lower alkoxy" includes both branched and straight-chain alkoxy of 1 to 6 carbons and includes for instance, methoxy, ethoxy, isopropoxy, t-butoxy, n-hexoxy and the like.

The term "halogen" includes the groups chloro, and bromo.

The term "a ring containing 4 to 6 carbon atoms" includes 1-piperidinyl, 1-pyrrolidinyl and 1-azacycloheptyl.

The term "a compound selected from the group consisting of

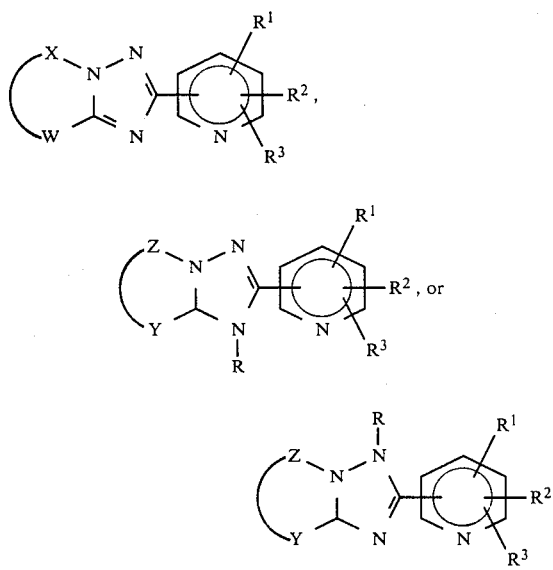

wherein

W and X are joined to form a heterocycle ring selected from the group consisting of

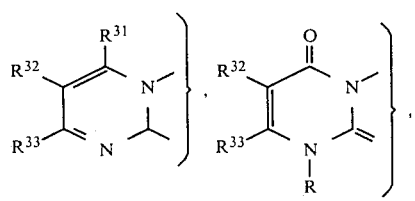

-continued

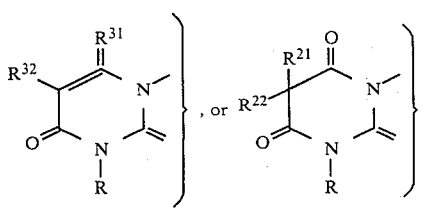

Y and Z are joined to form a heterocycle ring selected from the group consisting of

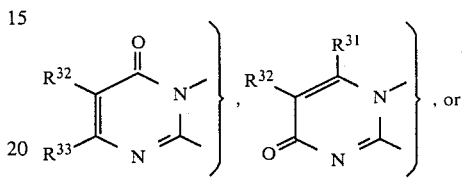

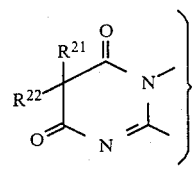

means the following compounds:
5,6,7-trisubstituted-2-(pyridinyl)-1,2,4-triazolo[1,5-a]pyrimidines (IA);
4,5,6-trisubstituted-2-(pyridinyl)-1,2,4-triazolo[1,5-a]pyrimidin-7(4H)-one (IB)';
3,5,6-trisubstituted-2-(pyridinyl)-1,2,4-triazolo[1,5-a]pyrimidin-7(3H)-ones (IC);
1,5,6-trisubstituted-2-(pyridinyl)-1,2,4-triazolo[1,5-a]pyrimidin-7(1H)-ones (ID);
4,6,7-trisubstituted-2-(pyridinyl)-1,2,4-triazolo[1,5-a]pyrimidin-5(4H)-ones (IE);
3,6,7-trisubstituted-2-(pyridinyl)-1,2,4-triazolo[1,5-a]pyrimidin-5(3H)-ones (IF);
1,5,6-trisubstituted-2-(pyridinyl)-1,2,4-triazolo[1,5-a]pyrimidin-5(1H)-ones (IG);
4,6,6-trisubstituted-2-(pyridinyl)-1,2,4-triazolo[1,5-a]pyrimidin-5,7(4H,6H)-diones (IH);
3,6,6-trisubstituted-2-(pyridinyl)-1,2,4-triazolo[1,5-a]pyrimidin-5,7(3H,6H)-diones (II);
1,6,6-trisubstituted-2-(pyridinyl)-1,2,4-triazolo[1,5-a]pyrimidin-5,7(1H,6H)-diones (IJ);

The term "pharmaceutically acceptable salts" includes the pharmaceutically acceptable acid addition salts of the compound of formula IA to IJ derived from a variety of organic and inorganic acids, such as sulfuric, phosphoric, hydrochloric, hydrobromic, sulfamic, citric, lactic, oleic, succinic, tartaric, cinnamic, acetic, benzoic, ascorbic and other organic and inorganic acids which form pharmaceutically acceptable addition salts.

The term 1,2,4-triazolo[1,5-a]pyrimidine means the group:

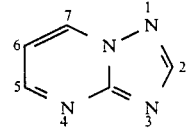

with the conventional numbering system shown therewith.

Thus the term 2-(4'-pyridinyl)-1,2,4-triazolo[1,5-a]pyrimidine means the group:

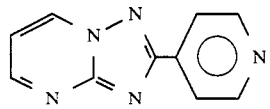

2'-Hydroxypyridinyl derivatives are tautomeric with 2-(1H)pyridinones as shown below:

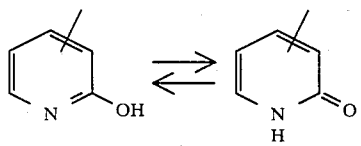

Throughout this disclosure, the term 2-(2'-hydroxypyridinyl) shall be taken to mean any of the above tautomers.

The term "pyridinyl" includes the 2-pyridinyl, 3-pyridinyl and 4-pyridinyl groups.

The term "4-methyl-2-(4'-pyridinyl)-1,2,4-triazolo[1,5-a]pyrimidin-7(4H)one" means the group:

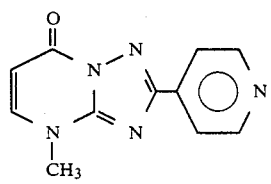

The compounds of the present invention have been found to increase cardiac contractility. As such, these compounds are useful in the treatment of congestive heart failure.

Preferred compounds of this invention are compounds represented by the formulas

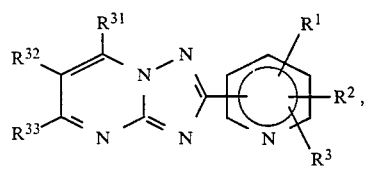

IA

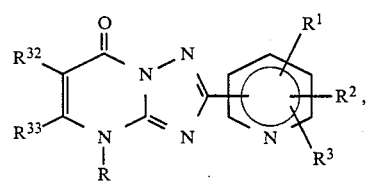

IB

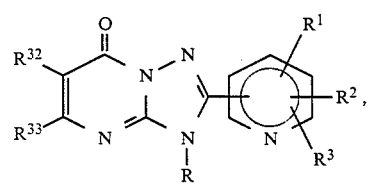

IC

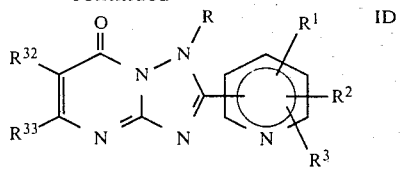

ID

Most preferred of the compounds of this invention are the compounds of IA.

As used herein, "pyridinyl groups" include pyridinyl and pyridinyl substituted with 1 to 3 substituents independently selected from halogen, lower alkyl, hydroxy, lower alkoxy and amino.

Preferred pyridinyl groups include 4'-pyridinyl and 4'-pyridinyl substituted with 1 to 3 substituents independently selected from halogen, lower alkyl, hydroxy, lower alkoxy and amino.

Another preferred pyridinyl group is 6'-hydroxy-3'-pyridinyl.

Most preferred pyridinyl groups are 4'-pyridinyl, 2'-methyl-4'-pyridinyl, 2'-hydroxy-4'-pyridinyl, and 6'-hydroxy-3'-pyridinyl.

$R^{31}, R^{32}$ and $R^{33}$ preferably are hydrogen, lower alkyl, hydroxy, cyano, —$NR^4R^5$ wherein $R^4$ is hydrogen, lower alkyl, or

wherein $R^6$ is lower alkyl, and $R^5$ is hydrogen, lower alkyl or together with $R^4$ are joined to form a ring which with the nitrogen contains 4 to 6 carbon atoms,

wherein $R^7$ is hydroxy, lower alkoxy or —$NR^8R^9$ wherein $R^8$ and $R^9$ are independently selected from hydrogen or lower alkyl.

Preferred $R^{31}, R^{32}, R^{33}$ and $R^6$ lower alkyl substituents include methyl, ethyl, n-propyl and isopropyl.

Preferred $R^4$ and $R^5$ groups are hydrogen and lower alkyl, most preferably, hydrogen.

$R^7$ is preferably —$NR^8R^9$ wherein $R^8$ and $R^9$ are independently hydrogen or lower alkyl.

Particularly preferred are compounds wherein $R^8$ and $R^9$ substituents are each hydrogen.

Preferred R, $R^{21}$ and $R^{22}$ groups are lower alkyl. Most preferably, R, $R^{21}$ and $R^{22}$ are each methyl.

DETAILED DESCRIPTION OF THE INVENTION

The compounds of this invention have been found to increase cardiac contractility. As such, the compounds of this invention are useful in the treatment of congestive heart failure.

The compounds were tested for their ability to increase cardiac contractility both in vitro and in vivo.

In vitro tests were conducted on left atria obtained from guinea pigs employing a modification of the method described in J. Pharmacol. Exp.Ther.217; 708–713 (1981). Increases in cardiac contractility were found at concentrations ranging from 32 μgm/ml to 1000 μgm/ml.

In vivo tests were conducted on open-chest barbiturated-anesthetized dogs employing the method described in J. Pharmacology Exp. Ther. 218, 444–452 (1981). Increases in cardiac contractility were generally found at dosage levels of 3.2 mg/kg to 10 mg/kg of body weight.

The present invention contemplates a method for increasing cardiac contractility in a patient requiring such treatment which comprises administering either orally or parenterally an amount of a compound of Formula A to C effective in increasing cardiac contractility.

Typically, a daily dosage regimen would generally be 0.5 to 5 gm/day administered orally and 0.1 to 2 gm/day administered parenterally. The specific dose to be administered is determined by the clinician considering various factors such as the particular compound employed, age and weight of the subject the severity of the disease and the individual's response. The daily dosage may be administered either singly or divided proportionally into several dosages.

The compounds are preferably administered either orally or parenterally with the preferred mode of administration dependent on the severity of the individual's condition. For example, with an individual suffering an acute case of congestive heart failure the preferred mode of administration would be parenterally, while for a chronic case of heart failure, the preferred mode of administration would be orally. The compounds may be combined with any suitable compatible pharmaceutically acceptable carrier and administered in a variety of formulations containing pharmaceutically acceptable excipients. The compounds may also be administered transdermally.

The methods of this invention are implemented using pharmaceutical compositions comprising a pharmaceutically acceptable carrier and an amount of a compound of formula A to C effective in increasing cardiac contractility.

In treating certain patients with the compounds of this invention, it is possible to include other pharmaceutically active ingredients in the same dosage unit.

The compounds of formula IA are conveniently prepared from 5-amino-3-pyridinyl-1,2,4-triazoles, II. The synthesis of these 1,2,4-triazoles is well known in the art and is described by LaMattina and Taylor, Journal of Organic Chemistry, 46, 4179–4182 (1981) and by Biemonn and Bratschneider, Monatshefte für Chemie, Bd 89/4-5, 603–610 (1958) which are incorporated herein by reference.

Reaction (1) is a conventional cyclization reaction and is described by Mosby, *Heterocyclic Systems with Bridgehead Nitrogen Atoms Part II*, 878–883 (Interscience Publishers, Inc., N.Y., 1961) and by Novinson et al, Journal of Medicinal Chemistry, 25, 420–426, (1982) which are incorporated herein by reference.

The cyclization of reaction (1) is accomplished by addition of an excess amount (approximately 3 equivalents) of the appropriate 1,3-dicarbonyl reagent, III, to the 5-amino-3-pyridinyl-1,2,4-triazole, II, to produce the 1,2,4-triazolo[1,5-a]pyrimidine as shown below:

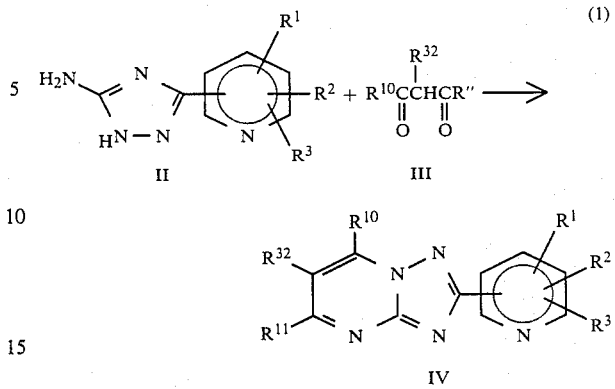

wherein $R^1$, $R^2$, $R^3$ and $R^{32}$ are as defined above and $R^{10}$ and $R^{11}$ are hydrogen, hydroxy, lower alkyl and lower alkoxy. If $R^{10}$ and/or $R^{11}$ are lower alkoxy, the cyclization proceeds with the displacement of the alkoxy group with the resultant $R^{10}$ and/or $R^{11}$ groups in IV being hydroxy.

The reaction is conducted in the liquid phase employing an inert organic solvent such as dimethylformamide, acetic acid, and ethanol. Preferably when $R^{10}$ and $R^{11}$ are hydrogen or lower alkyl, a catalytic amount ($\sim 0.05$ to 0.10 equivalents to the 3-pyridinyl-5-amino-1,2,4-triazole) of piperidine is added to the system in order to speed reaction completion. Alternatively, in lieu of a solvent, the reaction may be conducted neat. Reaction pressure is not critical and for convenience the reaction is generally conducted at atmospheric pressure. The reaction is generally conducted at from 50° to 180° C., although preferably below the boiling point of the dicarbonyl reagent, III, and is generally complete within ½ to 96 hours. The 2-(pyridinyl)-1,2,4-triazolo[1,5-a]pyrimidine, IV, is then isolated and purified by conventional procedures such as extraction, filtration, chromatography, distillation, or alternatively, can be used in succeeding reactions without isolation and/or purification.

The hydroxyl $R^{31}$, $R^{32}$ and $R^{33}$ groups are also readily converted to the halo groups by treatment with a halogenating agent such as phosphorous oxychloride or phosphorus oxybromide. The halo functionality preferably, chloro, is then readily converted to the corresponding amine by treatment with $R^4R^5NH$. Both of these reactions are known in the art and are described by Novinson et al, Journal of Medicinal Chemistry, 25, 420–426 (1982) and by Makisumi, Chem. Pharm. Bull. 9, 801–814 (1961).

Alternatively, the alkyl 7-amino-6-carboxylate may be prepared as described by L. Williams, J. Chem. Soc. 2222–2228 (1962).

The primary or secondary amine (eg $R^4$ and/or $R^5$=hydrogen) substituent is readily acylated by treatment with an appropriate acid halide as shown in reaction (2) below:

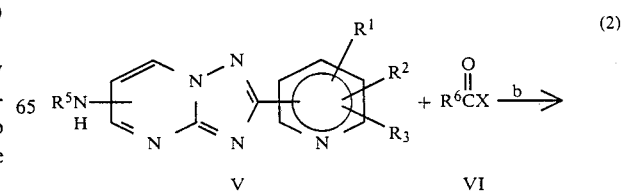

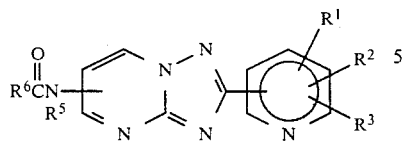

VII wherein $R^1$, $R^2$, $R^3$, $R^5$ and $R^6$ are as defined above, X is a halogen and b is a base.

The reaction is conducted by adding an essentially equimolar amount of the acid halide, VI, to V. The reaction is conducted in the liquid phase employing an anhydrous inert organic solvent such as chloroform, toluene and the like. An essentially equimolar amount of a base, b, is employed to scavenge the acid generated by the reaction. Preferably, an organic base such as pyridine, triethylamine and the like is employed. Alternatively, in lieu of a solvent, an excess of the organic base may be employed. Reaction pressure is not critical and for convenience the reaction is generally conducted at atmospheric pressure. The reaction is generally conducted at from 0° to 70° C. and is generally complete within 1 to 72 hours. The product VII, is then isolated and purified by conventional procedures such as extraction, filtration, chromatography, distillation and the like.

Compounds of formula IA to IG wherein $R^{32}$ is a carboxylic acid ester are readily prepared as shown in reaction (1) by addition of the appropriate alkyl 1,3-dicarbonyl 2-carboxylate reagent as described by Novinson et al, Journal of Medicinal Chemistry, 25, 420–426 (1982). The ester is readily hydrolyzed to the corresponding carboxylic acid by methods well known in the art.

Compounds of formula IA to IG wherein $R^{31}$ and/or $R^{33}$ are carboxylic acid groups are readily prepared from the corresponding halo starting material by addition of potassium cyanide in an inert solvent to form the cyano group. In order to increase the yield of the reaction a stoichrometric amount of a crown ether, such as dibenzo-18-crown-6 may be employed. The cyano is readily hydrolyzed to the carboxylic acid by acid hydrolysis which is known in the art. The carboxylic acid is readily converted to the corresponding esters by methods known in the art.

Alternatively, the 5- or 7-carboxylic acid are readily prepared as described by Shirakawa, CA 54:11039F.

The carboxylic acid ester is readily converted to the corresponding carboxamide by treatment with ammonia or the appropriate amine as shown in reaction (3) below:

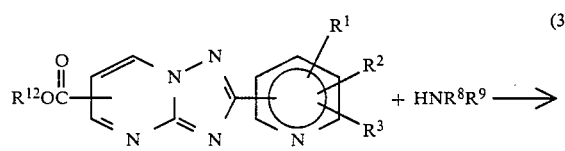

(3)

VIII   IX

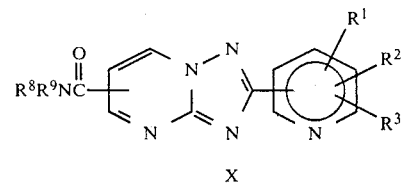

X wherein $R^1$, $R^2$, $R^3$, $R^8$ and $R^9$ are as defined above and $R^{12}$ is lower alkyl.

Reaction (3) can be accomplished by adding an excess of ammonia or the appropriate amine, IX to compound VIII. The reaction is conducted in the liquid phase employing an inert hydroxylic solvent, water or a mixture of the hydroxylic solvent and water as the solvent. Alternatively, in lieu of a solvent, an excess of the amine, IX, is employed. The reaction is generally conducted at pressures equal to or greater than atmospheric pressure and is generally complete within 72 hours. The resulting amide, X, can then be isolated and purified by conventional procedures such as extraction, distillation, chromotagraphy, filtration, or alternatively, can be used in succeeding reaction without isolation and/or purification.

The cyano derivatives may be converted to the carboxamidine group as shown in reaction (4) below:

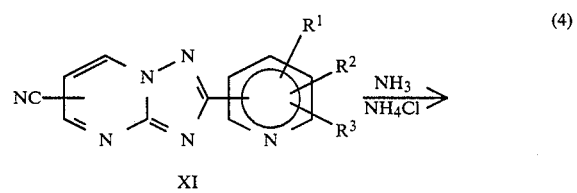

XI

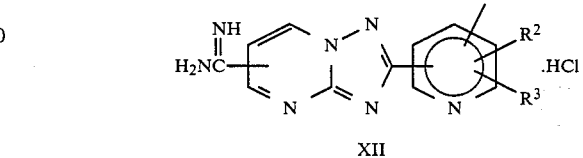

XII wherein $R^1$, $R^2$ and $R^3$ are as defined above.

The reaction is known in art and is described by F. C. Schaefer and A. P. Krapcho, Journal of Organic Chemistry, 27, 1255–1258 (1962) which is incorporated herewith by reference. The reaction is accomplished by treating the cyano derivative, XI, with liquid ammonia and ammonium chloride in a steel bomb at elevated temperatures (80° C.). The product, XII, is then isolated and purified by conventional procedures such as extraction, chromatography, filtration and the like.

The cyano derivative may also be converted to the thiocarboxamide group as shown in reaction (5) below:

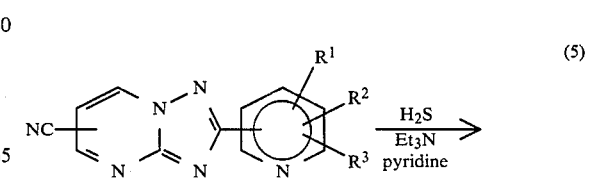 (5)

XI

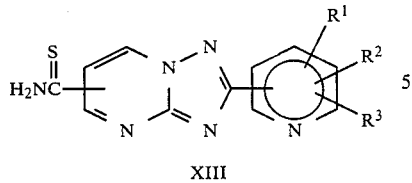

XIII wherein $R^1$, $R^2$ and $R^3$ is as defined above.

The reaction is known in the art and is described by A. C. S. Fairfull et al., Journal of the Chemical Society, 742–744 (1952). The reaction is accomplished by treating the cyano derivative, XI, with hydrogen sulfide and triethylamine in pyridine at or above room temperature. The product, XIII, can be isolated and purified by conventional procedures such as extraction, distillation, chromatography filtration and the like.

Selective modification of the substituents at the 5, 6 and 7 positions of the 1,2,4-triazolo[1,5-a]pyrimidines is known in the art and is well illustrated by Makisumi, Chem. Pharm. Bull. 9, 801–814 (1961).

The 7-hydroxy-2-(pyridinyl)-1,2,4-triazolo[1,5-a]pyrimidines are tautomeric with the 2-(pyridinyl)-1,2,4-triazolo[1,5-a]pyrimidin-7(4H)one, the 2-(pyridinyl)-1,2,4-triazolo[1,5-a]pyrimidin-7(3H)one, and the 2-(pyridinyl)-1,2,4-triazolo[1,5-a]pyrimidin-7(1H)-one as shown below:

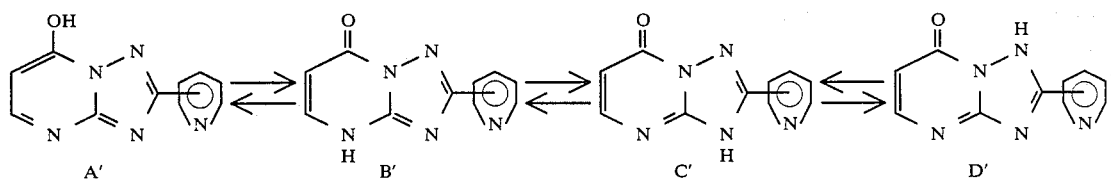

throughout this specification, the term 7-hydroxy-2-(pyridinyl)-1,2,4-triazolo[1,5-a]pyrimidines is used to mean any of the above tautomers.

The 5-hydroxy-2-(pyridinyl)-1,2,4-triazolo[1,5-a]pyrimidines are tautomeric with the 2-(pyridinyl)-1,2,4-triazolo[1,5-a]pyrimidin-5(4H)-ones, 2-(pyridinyl)-1,2,4-triazolo[1,5-a]pyrimidin-5(3H)-ones and the 2-(pyridinyl)-1,2,4-triazolo[1,5-a]pyrimidin-5(1H)-ones as shown below:

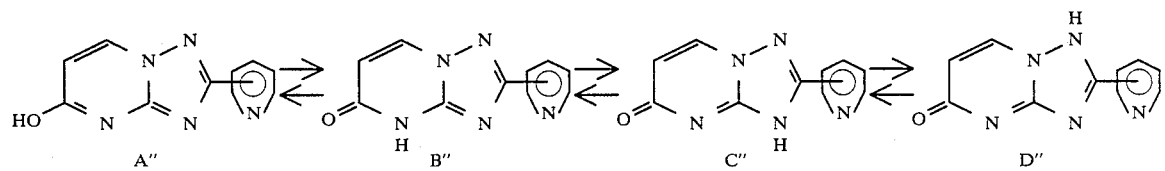

Throughout this specification, the term 5-hydroxy-2-(pyridinyl)-1,2,4-triazolo[1,5-a]pyrimidine shall be taken to mean any of the above tautomers.

The 4-substituted-1,2,4-triazolo[1,5-a]pyrimidin-5(4H) or 7(4H)ones, B' and B'', the 3-substituted-1,2,4-triazolo[1,5-a]pyrimidin-5(3H) or 7(3H)ones, C' and C'', and the 1-substituted-1,2,4-triazolo[1,5-a]pyrimidin-5(1H) or 7(1H) ones, D' and D'' can be "locked in" to their tautomeric structure by alkyl substitution of the corresponding 4, 3 and 1 nitrogen of the ring system.

Preparation of the compounds of formulas IB and IE, the 4-substituted-1,2,4-triazolo[1,5-a]pyrimidin-7(1H) or -5(1H)one, is accomplished by addition of an alkyl 3-keto-1-carboxylate reagent, XV, to a 5-N-alkylamino-3-pyridinyl-1,2,4-triazole, XIV, as shown in reaction (6) below:

wherein R, $R^1$, $R^2$, $R^3$ and $R^{10}$ are as defined above, and $R^{23}$ is lower alkyl.

The reaction is conducted as described for reaction (1) above. Preferably the 5-one is prepared by conducting reaction (6) neat while the 7-one is preferably prepared by conducting reaction (6) in acetic acid. The substituent $R^{10}$ may also be modified as described above.

Methods for the preparation of 5-N-alkylamino-3-substituted-1,2,4-triazole, XX, and 5-amino-3-substituted-4-alkyl-1,2,4 triazole, XIX, are described by E. Akerblom, Acta Chemica Scandinavica, 19, 1135–1141 (1965).

These products are conveniently prepared from the pyridinyl carbohydrazide, XVI, as shown in reactions (7) and (8) below:

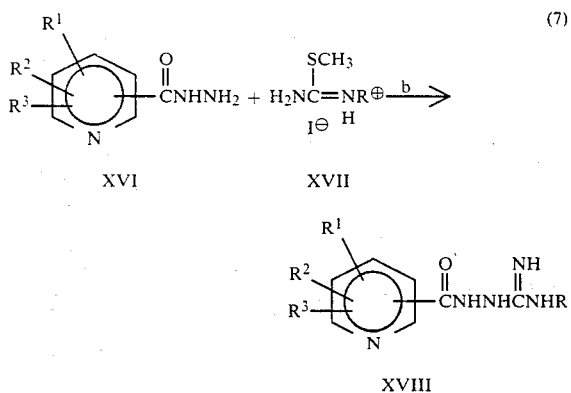

(7)

XVI   XVII

XVIII wherein R, $R^1$, $R^2$ and $R^3$ are as defined above; and b is a base.

(8)

XVIII

XIX

XX

Reaction (7) is conducted by adding an essentially equimolar amount of the pyridinyl carbohydrazide, XVI, to XVII. The reaction is conducted in the liquid phase employing a suitable solvent such as water, dimethylformamide and the like. An essentially equimolar amount of a base is added to the system to scavenge the acid present. Preferably, the reaction is conducted in water employing sodium hydroxide as the base. Reaction pressure is not critical and for convenience the reaction is generally conducted at atmospheric pressure. The reaction is generally conducted at from 0° to 60° C., although preferably at room temperature, and is generally complete within 24 to 96 hours. The product, XVIII, may than be isolated and purified by conventional procedures such as extraction, filtration, chromatography, distillation, or alternatively, can be used in reaction (8) without isolation and/or purification.

Reaction (8) may be conducted by heating XVIII in an appropriate solvent to accomplish cyclization. Preferably the starting material, XVIII, is heated in dimethylformamide. Reaction pressure is not critical and for convenience the reaction is generally conducted at atmospheric pressure. The reaction is generally complete within 1 to 24 hours and produces a mixture of the 5-amino-3-pyridinyl-4-alkyl-1,2,4-triazole, XIX, and 5-N-alkylamino-3-pyridinyl-1,2,4-triazole, XX. The mixture may be readily separated by chromatography, distillation and the like. Preferably, a greater yield of XX is obtained by employing a stoichiometric amount of a base such as sodium hydroxide.

Preparation of the compounds of formulas IC and IF, the 3-substiuted-2-pyridinyl-1,2,4-triazolo[1,5-a]pyrimidin5(3H) or 7(3H)-one, is accomplished by addition of an alkyl 3-keto-1-carboxylate reagent, XV, to a 5-amino-3-(pyridinyl)-4-alkyl-1,2,4-triazole, XIX, as shown in reaction (10) below:

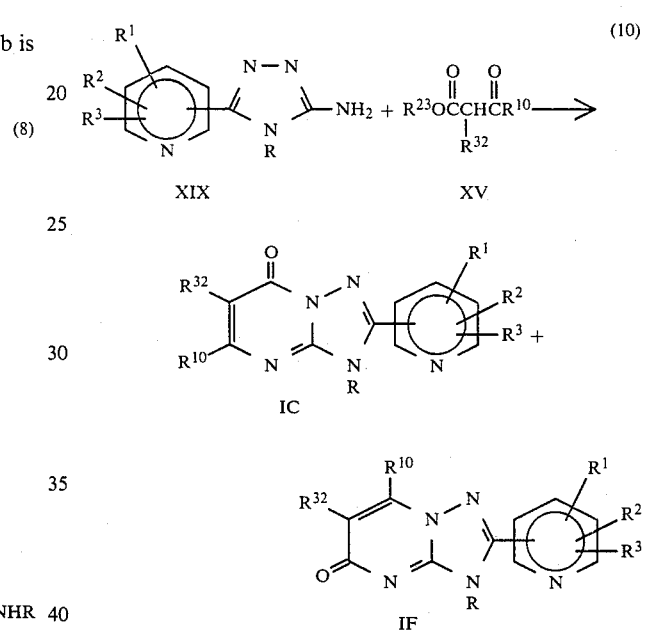

(10)

XIX   XV

IC

IF wherein R, $R^1$, $R^2$, $R^{10}$, and $R^{23}$ are as defined above.

The reaction is accomplished as described for reaction (1) above. Preferably the 5-one is prepared by conducting reaction (1) neat while the 7-one is preferably prepared by conducting reaction (1) in acetic acid. The substituent $R^{10}$ may also be modified as described above.

Preparation of the compounds of formulas ID and IG, the 1-substituted-2-(pyridinyl)-1,2,4-triazolo[1,5-a]pyrimidin-7-(1H) or 5-(1H)-one, may be accomplished by addition of an alkyl 3-keto-1-carboxylate reagent, XV, to a 1-alkyl-3-amino-5-pyridinyl-1,2,4-triazole, XXI, as shown in reaction (11) below:

(11)

XXI   XV

-continued

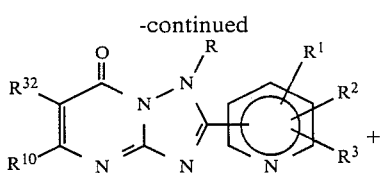

ID

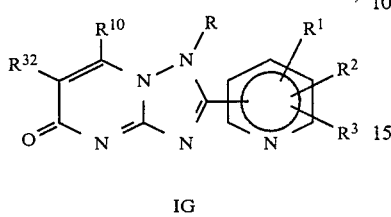

IG wherein R, $R^1$, $R^2$, $R^{10}$, and $R^{23}$ are as defined above.

The reaction is accomplished as described for reaction (1) above. Preferably the 5-one is prepared by conducting reaction (1) neat while the 7-one is preferably prepared by conducting reaction (1) in acetic acid. The substituent $R^{10}$ may also be modified as described above.

The 1-alkyl-3-amino-5-pyridinyl-1,2,4-triazole may be readily prepared from the corresponding 3-amino-5-pyridinyl-1,2,4-triazole under alkylating conditions. For instance, reaction of 3-amino-5-pyridinyl-1,2,4-triazole with sodium hydride followed by addition of methyl iodide yields the 1-methyl-3-amino-5-pyridinyl-1,2,4-triazole plus other isomers. Separation of the desired product may be readily accomplished by chromatography, distillation and the like.

Compounds of Formula IH, the 4-substituted-2-pyridinyl 1,2,4-triazolo[1,5-a]pyrimidin-5,7(4H,6H)-dione, may be readily prepared by addition of a dialkyl 1,3-dicarboxylate reagent, XXII, to the 5-N-alkylamino-3-pyridinyl-1,2,4-triazole, XX, as shown in reaction (12) below:

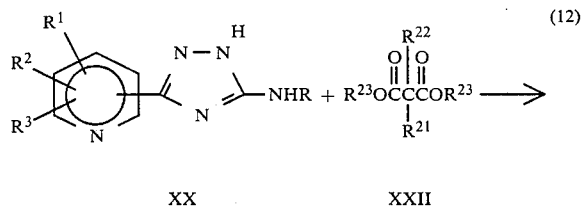

(12)

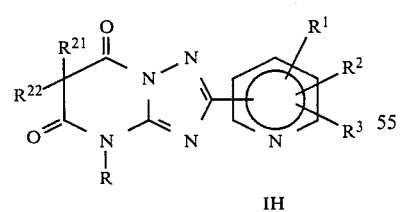

IH wherein R, $R^1$, $R^2$, $R^3$, $R^{21}$, $R^{22}$ and $R^{23}$ are as defined above.

The reaction is accomplished as described for reaction (1) above except that the reaction is conducted in ethanol and a stoichiometric amount of a base, such as sodium ethoxide, is employed.

Compounds of Formula II, the 3-substituted-2-pyridinyl-1,2,4-triazolo[1,5-a]pyrimidin-5,7-(3H, 6H)-dione, may be readily prepared by addition of a dialkyl 1,3-dicarboxylate reagent, XXII, to a 5-amino-3-(pyridinyl)-4-alkyl-1,2,4-triazole, XIX, as shown in reaction (13) below:

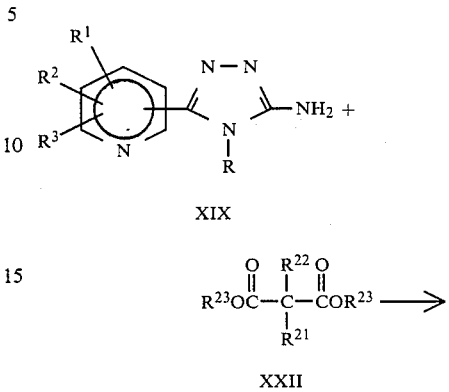

XIX

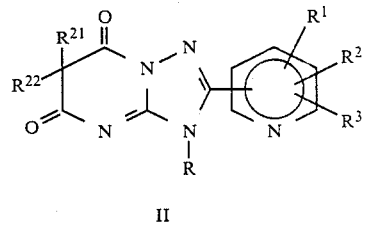

XXII

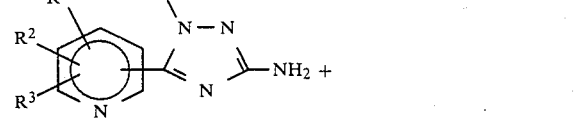

II wherein R, $R^1$, $R^2$, $R^3$, $R^{21}$, $R^{22}$ and $R^{23}$ are as defined above.

The reaction is accomplished as described for reaction (1) above except that the reaction is conducted in ethanol and a stoichrometric amount of a base, such as sodium ethoxide is employed.

The compounds of Formula IJ, the 1-substituted-2-pyridinyl-1,2,4-triazolo[1,5-a]pyrimidin-5,7-(1H, 6H)-dione, may be readily prepared by addition of a dialkyl 1,3-dicarboxylate reagent, XXII, to a 1-alkyl-3-amino-5-(pyridinyl)-1,2,4-triazole, XXI, as shown in reaction (14) below:

(14)

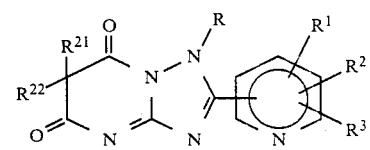

XXI

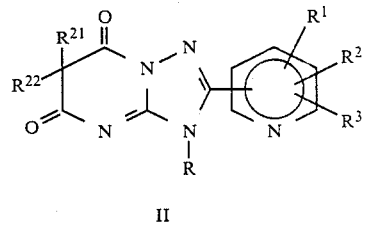

XXII

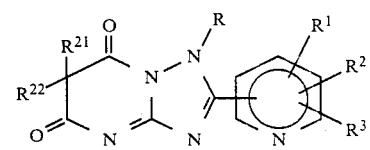

IJ wherein R, $R^1$, $R^2$, $R^3$, $R^{21}$, $R^{22}$ and $R^{23}$ are as described above.

The reaction is accomplished as described for reaction (1) above except that the reaction is conducted in ethanol and a stoichrometric amount of a base, such as sodium ethoxide is employed.

The following non-limiting examples describe in detail the preparation of the compounds and compositions of the present invention. As used herein the term "room temperature" refers to about 20° to 25° C. Unless otherwise stated, all temperature and temperature ranges are in degrees Celsius.

EXAMPLE 1

Preparation of
5,7-Dimethyl-2-(4'-pyridinyl)-1,2,4-triazolo[1,5-a]pyrimidine

Add 24.18 gm of 5-amino-3-(4'-pyridinyl)-1,2,4-triazole to 450 ml of N,N-dimethylformamide containing 50 ml of 2,4-pentanedione and 1.0 ml of piperidine. Heat the system in an oil bath at 130° until the reaction is complete (60–72 hours) as determined by thin layer chromatography on silica gel using ethyl acetate-methanol (10:1) as the elutant. Stop the reaction and remove the solvent by stripping to yield a residue. Dissolve the residue in hot ethanol, treat with activated carbon and filter. Cool the filtrate, collect the product by filtration and recrystallize from ethanol. Dry the product under reduced pressure to give 5,7-dimethyl-2-(4'-pyridinyl)-1,2,4-triazolo[1,5-a]pyrimidine.

EXAMPLE 2

Preparation of
5,7-dimethyl-2-(3'-methyl-4'-pyridinyl)-1,2,4-triazolo[1,5-a]pyrimidine Add 0.54 gm of 5-amino-3-(3-methyl-4-pyridinyl)-1,2,4-triazole and 0.31 ml of 2,4-pentanedione to 5 ml of glacial acetic acid. Heat the system to reflux for 20 hours. Stop the reaction and remove the solvent by stripping to give a solid residue. Wash the solid residue with ethyl acetate. Suspend the solid in water and make the solution basic with 1N NaOH to give the 5,7-dimethyl-2-(3'-methyl-4'-pyridinyl)-1,2,4-triazolo[1,5-a]pyrimidine.

EXAMPLE 3

Preparation of
7-hydroxy-5-methyl-2-(4'-pyridinyl)-1,2,4-triazolo[1,5-a]pyrimidine Add 2.71 gm of 5-amino-3-(4'-pyridinyl)-1,2,4-triazole and 2.09 gm of ethylacetoacetate to 7 ml of ethanol and 35 ml of glacial acetic acid. Heat the system to reflux for 17 hours. Stop the reaction and cool the system. Filter the white precipitate. Wash the precipitate with cold ethanol and ether and then dry under reduced pressure to give 7-hydroxy-5-methyl-2-(4'-pyridinyl)-1,2,4-triazolo[1,5-a]pyrimidine.

EXAMPLE 4

Preparation of
5,7-dimethyl-2-(2'-hydroxy-4'-pyridinyl)-1,2,4-triazolo[1,5-a]pyrimidine Add 26.6 gm of 3-(2'-hydroxypyridinyl)-5-amino-1,2,4-triazole to 450 ml of N,N-dimethylformamide containing 55 ml of 2,4-pentanedione and 1.0 ml of piperdine. Heat the system in an oil bath at 130° until the reaction is complete (60–72 hours) as determined by thin layer chromatography on silica gel using ethyl acetate-methanol (10:1) as the eluant. Stop the reaction and remove the solvent by stripping to yield the 5,7-dimethyl-2-(2'-hydroxy-4'-pyridinyl)-1,2,4-triazolo[1,5-a]pyrimidine.

Similarly, by following the same procedures as outlined in Examples 1 to 4 above and employing the appropriate reagents, the following compounds of this invention may be prepared:

2-(4'-pyridinyl)-1,2,4-triazolo[1,5-a]pyrimidine;
2-(2'-hydroxy-4'-pyridinyl)-1,2,4-triazolo[1,5-a]pyrimidine;
2-(2'-bromo-3'-hydroxy-4'-pyridinyl)-1,2,4-triazolo[1,5-a]pyrimidine;
5-hydroxy-7-methyl-2-(4'-pyridinyl)-1,2,4-triazolo[1,5-a]pyrimidine;
2-(3'-pyridinyl)-1,2,4-triazolo[1,5-a]pyrimidine;
2-(6'-hydroxy-3'-pyridinyl)-1,2,4-triazolo[1,5-a]pyrimidine;
2-(2'-bromo-6'-hydroxy-3'-pyridinyl)-1,2,4-triazolo[1,5-a]pyrimidine;
5,7-dimethyl-2-(3'-pyridinyl)-1,2,4-triazolo[1,5-a]pyrimidine;
5-hydroxy-7-methyl-2-(3'-pyridinyl)-1,2,4-triazolo[1,5-a]pyrimidine;
5,7-dihydroxy-2-(2'-pyridinyl)-1,2,4-triazolo[1,5-a]pyrimidine;
2-(2'-pyridinyl)-1,2,4-triazolo[1,5-a]pyrimidine;
2-(6'-hydroxy-2'-pyridinyl)-1,2,4-triazolo[1,5-a]pyrimidine;
2-(4'-bromo-6'-hydroxy-2'-pyridinyl)-1,2,4-triazolo[1,5-a]pyrimidine;
5,7-dimethyl-2-(2'-pyridinyl)-1,2,4-triazolo[1,5-a]pyrimidine; and
5-hydroxy-7-methyl-2-(2'-pyridinyl)-1,2,4-triazolo[1,5-a]pyrimidine.

EXAMPLE 5

Preparation of
7-chloro-5-methyl-2-(4'-pyridinyl)-1,2,4-triazolo[1,5-a]pyrimidine Add 5 ml of phosphorus oxychloride to 200 mg of 7-hydroxy-5-methyl-2-(4'-pyridinyl)-1,2,4-triazolo[1,5-a]pyrimidine and heat the system to reflux for 2 hours. Distill off the excess phosphorus oxychloride in vacuo and pour the residual liquid into ice. Add 1N NaOH and extract the product with ether. Dry the ether over magnesium sulfate and concentrate the ether in vacuo to give 7-chloro-5-methyl-2-(4'-pyridinyl)-1,2,4-triazolo[1,5-a]pyrimidine.

EXAMPLE 6

Preparation of
7-amino-5-methyl-2-(4'-pyridinyl)-1,2,4-triazolo[1,5-a]pyrimidine Add 3.0 gm of 7-chloro-5-methyl-2-(4'-pyridinyl)-1,2,4-triazolo[1,5-a]pyrimidine to 100 ml of 20% $NH_3$ in ethanol. Heat the system in a sealed tube at 160° C. for 8 hours. Remove the solvent by stripping to give 7-amino-5-methyl-2-(4'-pyridinyl)-1,2,4-triazolo[1,5-a]pyrimidine.

EXAMPLE 7

Preparation of
7-N-acetylamino-5-methyl-2-(4'-pyridinyl)-1,2,4-triazolo[1,5-a]pyrimidine Add 21.4 gm of 7-amino-5-methyl-2-(4'-pyridinyl)-1,2,4-triazolo[1,5-a]pyrimidine to 400 ml of N,N-dimethylformamide containing 7.8 gm of acetyl chloride and 7.9 gm of pyridine. Stir the reaction at room temperature for 16 hours. Filter the solution and remove the solvent by stripping to give 7-N-acetylamino-5-methyl-2-(4'-pyridinyl)-1,2,4-triazolo[1,5-a]pyrimidine.

Similarly, by following the same procedures as outlined in the examples above and employing the appropriate reagents, the following compounds of this invention may be prepared:

5-amino-2-(2'-hydroxy-4'-pyridinyl)-1,2,4-triazolo[1,5-a]pyrimidine;
5-N-acetylamino-6,7-dimethyl-2-(3'-amino-4'-pyridinyl)-1,2,4-triazolo[1,5-a]pyrimidine;
7-N,N-dimethylamino-2-(4'-pyridinyl)-1,2,4-triazolo[1,5-a]pyrimidine;
7-piperdinyl-2-(4'-pyridinyl)-1,2,4-triazolo[1,5-a]pyrimidine;
6,7-dichloro-2-(4'-pyridinyl)-1,2,4-triazolo[1,5-a]pyrimidine;
7-N,N-di-n-propylamino-5-ethyl-2-(4'-pyridinyl)-1,2,4-triazolo[1,5-a]pyrimidine;
6-N,N-diethyl-2-(4'-pyridinyl)-1,2,4-triazolo[1,5-a]pyrimidine;
6-N-methyl, N-acetylamino-2-(4'-pyridinyl)-1,2,4-triazolo-[1,5-a]pyrimidine;
5-amino-2-(2'-hydroxy-3'-pyridinyl)-1,2,4-triazolo[1,5-a]pyrimidine;
5-N-acetylamino-6,7-dimethyl-2-(6-amino-3'-pyridinyl)-1,2,4-triazolo[1,5-a]pyrimidine;
7-N,N-dimethylamino-2-(3'-pyridinyl)-1,2,4-triazolo[1,5-a]pyrimidine;
7-piperidinyl-2-(3'-pyridinyl)-1,2,4-triazolo[1,5-a]pyrimidine;
6,7-dichloro-2-(3'-pyridinyl)-1,2,4-triazolo[1,5-a]pyrimidine;
7-N,N-di-n-propylamino-6-ethyl-2-(3'-pyridinyl)-1,2,4-triazolo[1,5-a]pyrimidine;
6-N,N-diethylamino-2-(3'-pyridinyl)-1,2,4-triazolo[1,5-a]pyrimidine;
6-N-methyl, N-acetylamino-2-(3'-pyridinyl)-1,2,4-triazolo[1,5-a]pyrimidine;
5-amino-2-(3'-hydroxy-2'-pyridinyl)-1,2,4-triazolo[1,5-a]pyrimidine;
5-N-acetylamino-6,7-dimethyl-2-(3'-amino-2'-pyridinyl)-1,2,4-triazolo[1,5-a]pyrimidine;
7-N,N-dimethylamino-2-(2'-pyridinyl)-1,2,4-triazolo[1,5-a]pyrimidine;
7-piperidinyl-2-(2'-pyridinyl)-1,2,4-triazolo[1,5-a]pyrimidine;
6,7-dichloro-2-(2'-pyridinyl)-1,2,4-triazolo[1,5-a]pyrimidines;
7-N,N-di-n-propylamino-5-ethyl-2-(2'-pyridinyl)-1,2,4-triazolo[1,5-a]pyrimidine;
6-N,N-diethylamino-2-(2'-pyridinyl)-1,2,4-triazolo[1,5-a]pyrimidine; and
6-N-methyl, N-acetylamino-2-(2'-pyridinyl)-1,2,4-triazolo[1,5-a]pyrimidine.

EXAMPLE 8

Preparation of
7-cyano-5-methyl-2-(4'-pyridinyl)-1,2,4-triazolo[1,5-a]pyrimidine Add 3.60 gm of dibenzo-18-crown-6 (dibenzo-1,4,7,10,13,16-hexaoxacycloactadeca-2,11-diene) to 200 ml of dimethoxyethane containing 0.57 gm of potassium cyanide and 2.33 gm of 7-chloro-5-methyl-2-(4'-pyridinyl)-1,2,4-triazolo[1,5-a]pyrimidine. Heat the system at reflux for 16 hours. Wash the organic solution twice with water and remove the solvent by stripping. Separate the 7-cyano-5-methyl-2-(4'-pyridinyl)-1,2,4-triazolo[1,5-a]pyrimidine by chromatography.

EXAMPLE 9

Preparation of Methyl
5-methyl-2-(4'-pyridinyl)-1,2,4-triazolo[1,5-a]pyrimidine-7-carboxylate Add 2.24 gm of 5-methyl-7-cyano-1,2,4-triazolo[1,5-a]pyrimidine to 100 ml of methanol containing 10 ml of concentrated hydrochloric acid. Reflux the system until the reaction is complete (as indicated by thin layer chromatography (TLC)). Neutralize the system nd remove the solvent by stripping to yield methyl 5-methyl-2-(4'-pyridinyl)-1,2,4-triazolo[1,5-a]pyrimidine-7-carboxylate.

EXAMPLE 10

Preparation of
5-methyl-2-(4'-pyridinyl)-1,2,4-triazolo[1,5-a]pyrimidine-7-carboxylic acid Add 2.57 gm of methyl 5-methyl-2-(4'-pyridinyl)-1,2,4-triazolo[1,5-a]pyrimidine-7-carboxylate to 100 ml of methanol containing 10 ml of 2N sodium hydroxide solution. Heat the system at reflux until complete (as indicated by TLC). Filter the system and then neutralize the solution with acetic acid. Remove the solvent to give the title compound.

EXAMPLE 11

Preparation of
5-methyl-2-(4'-pyridinyl)-1,2,4-triazolo[1,5-a]pyrimidine-7-carboxamide Add 2.50 gm of methyl 5-methyl-2-(4'-pyridinyl)-1,2,4-triazolo[1,5-a]pyrimidine-7-carboxylate to 50 ml of 20% ammonia in methanol in a steel bomb cooled to 0° to 5° C. Heat the system in an oil bath at 65° C. for 48 hours. Remove the solvent by stripping to yield 5-methyl-2-(4'-pyridinyl)-1,2,4-triazolo[1,5-a]pyrimidine-7-carboxamide.

EXAMPLE 12

Preparation of Ethyl
7-hydroxy-2-(4'-pyridinyl)-1,2,4-triazolo[1,5-a]pyrimidine-6-carboxylate Add 3.24 gm of 5-amino-3-(4'-pyridinyl)-1,2,4-triazole to 50 ml of glacial acetic acid containing 4.48 ml of diethyl ethoxymethylene malonate. Heat the system to reflux for 20 hours. Cool the system and filter the solid product. Chromatograph the solid on a column of silica gel using chloroform:methanol:ammonium hydroxide (200:20:2) to give the title compound. Similarly, by following the same procedures as outlined in the Examples above and employing the appropriate reagents, the following compounds of this invention may be prepared:

5-cyano-2-(3'-methoxy-2'-methyl-4'-pyridinyl)-1,2,4-triazolo[1,5-a]pyrimidine;
N-methyl 2-(4'-pyridinyl)-1,2,4-triazolo[1,5-a]pyrimidine-7-carboxamide;
2-(4'-pyridinyl)-1,2,4-triazolo[1,5-a]pyrimidine-7-carboxamide;
2-(4'-pyridinyl)-1,2,4-triazolo[1,5-a]pyrimidine-6-carboxamide;
7-hydroxy-2-(4'-pyridinyl)-1,2,4-triazolo[1,5-a]pyrimidine-6-carboxamide;
2-(4'-pyridinyl)-1,2,4-triazolo[1,5-a]pyrimidine-5-carboxamide;
N-Ethyl 2-(4'-pyridinyl)-1,2,4-triazolo[1,5-a]pyrimidine-5-carboxamide;
N-Methyl-2-(4'-pyridinyl)-1,2,4-triazolo[1,5-a]pyrimidine-6-carboxamide;
n-propyl 2-(4'-pyridinyl)-1,2,4-triazolo[1,5-a]pyrimidine-5-carboxylate;
n-hexyl 2-(4'-pyridinyl)-1,2,4-triazolo[1,5-a]pyrimidine-5-carboxylate;
t-butyl 2-(2'-hydroxy-3'-methyl-4'-pyridinyl)-1,2,4-triazolo[1,5-a]pyrimidine-5-carboxylate;
isopropyl 7-methyl-2-(4'-pyridinyl)-1,2,4-triazolo[1,5-a]pyrimidine-5-carboxylate;
5-ethyl 2-(4'-pyridinyl)-1,2,4-triazolo[1,5-a]pyrimidine-7-carboxylic acid;
5-cyano-2-(4'-methoxy-2'-methyl-3'-pyridinyl)-1,2,4-triazolo[1,5-a]pyrimidine;
N-methyl-2-(3'-pyridinyl)-1,2,4-triazolo[1,5-a]pyrimidine-7-carboxamide;
2-(3'-pyridinyl)-1,2,4-triazolo[1,5-a]pyrimidine-7-carboxamide;
2-(3'-pyridinyl)-1,2,4-triazolo[1,5-a]pyrimidine-6-carboxamide;
2-(3'-pyridinyl)-1,2,4-triazolo[1,5-a]pyrimidine-5-carboxamide;
Ethyl 2-(3'-pyridinyl)-1,2,4-triazolo[1,5-a]pyrimidine-7-carboxylate;
Methyl 2-(3'-pyridinyl)-1,2,4-triazolo[1,5-a]pyrimidine-6-carboxylate;
n-propyl 2-(3'-pyridinyl)-1,2,4-triazolo[1,5-a]pyrimidine-5-carboxylate;
n-hexyl 2-(3'-pyridinyl)-1,2,4-triazolo[1,5-a]pyrimidine-5-carboxylate;
t-butyl 2-(2'-hydroxy-4'-methyl-3'-pyridinyl)-1,2,4-triazolo[1,5-a]pyrimidine-5-carboxylate;
isopropyl 7-methyl-2-(3'-pyridinyl)-1,2,4-triazolo[1,5-a]pyrimidine-5-carboxylate;
5-methyl-2-(3'-pyridinyl)-1,2,4-triazolo[1,5-a]pyrimidine-7-carboxylic acid;
5-cyano-2-(3'-methoxy-6'methyl-2'-pyridinyl)-1,2,4-triazolo[1,5-a]pyrimidine;
N-methyl 2-(2'-pyridinyl)-1,2,4-triazolo[1,5-a]pyrimidine-7-carboxamide;
2-(2'-pyridinyl)-1,2,4-triazolo[1,5-a]pyrimidine-7-carboxamide;
2-(2'-pyridinyl)-1,2,4-triazolo[1,5-a]pyrimidine-6-carboxamide;
2-(2'-pyridinyl)-1,2,4-triazolo[1,5-a]pyrimidine-5-carboxamide;
Ethyl 2-(2'-pyridinyl)-1,2,4-triazolo[1,5-a]pyrimidine-7-carboxylate;
Methyl 2-(2'-pyridinyl)-1,2,4-triazolo[1,5-a]pyrimidine-6-carboxylate;
n-propyl 2-(2'-pyridinyl)-1,2,4-triazolo[1,5-a]pyrimidine-5-carboxylate;
n-hexyl 2-(2'-pyridinyl)-1,2,4-traizolo[1,5-a]pyrimidine-5-carboxylate;
t-butyl 2-(2'-hydroxy-3'-methyl-2'-pyridinyl)-1,2,4-triazolo[1,5-a]pyrimidine-5-carboxylate;
isopropyl 7-methyl-2-(2'-pyridinyl)-1,2,4-triazolo[1,5-a]pyrimidine-5-carboxylate; and
5-methyl-2-(2'-pyridinyl)-1,2,4-triazolo[1,5-a]pyrimidine-7-carboxylate.

EXAMPLE 13

Preparation of 5-methyl-2-(4'-pyridinyl)-1,2,4-triazolo[1,5-a]pyrimidine-7-carboxamidine hydrochloride Add 2.50 gm of 7-cyano-5-methyl-2-(4'-pyridinyl)-1,2,4-triazolo[1,5-a]pyrimidine to 0.53 gm of ammonium chloride in liquid ammonia in a steel bomb. Heat the system to 80° C. for 24 hours. Cool the system to room temperature and remove the ammonia. Isolate the 5-methyl-2-(4'-pyridinyl)-1,2,4-triazolo[1,5-a]-pyrimidine-7-carboxamidine hydrochloride.

EXAMPLE 14

Preparation of 5-methyl-2-(4'-pyridinyl)-1,2,4-triazolo[1,5-a]pyrimidine-7-thiocarboxamide Dissolve 2.5 gm. of 7-cyano 5-methyl-2-(4'-pyridinyl)1,2,4-triazolo[1,5-a]pyrimidine in 25 gm of pyridine. Add 1.5 ml of triethylamine to the system. Cool the system to 0° to 5° C. and treat the system with hydrogen sulfide gas until the reaction is complete as indicated by thin layer chromatography. Isolate the 5-methyl-2-(4'-pyridinyl)-1,2,4-triazolo[1,5-a]pyrimidine-4-thiocarboxamide.

Similarly by following the same procedures as outlined in the Examples above and employing the appropriate reagents, the following compounds of this invention may be prepared:
5-methyl-2-(3'-pyridinyl)-1,2,4-triazolo[1,5-a]pyrimidine-7-carboxamidine hydrochloride;
5-methyl-2-(3'-pyridinyl)-1,2,4-triazolo[1,5-a]pyrimidine-7-thiocarboxamide;
5-methyl-2-(2'-pyridinyl)-1,2,4-triazolo[1,5-a]pyrimidine-7-carboxamidine hydrochloride; and
5-methyl-2-(2'-pyridinyl)-1,2,4-triazolo[1,5-a]pyrimidine-7-thiocarboxamide.

EXAMPLE 15

Preparation 3-(4'pyridinyl)-5-N-methylamino-1,2,4-triazole and 4-methyl-5-amino-3-(4'-pyridinyl)-1,2,4-triazole (a) Add 13.9 gm of 4-pyridinyl carbohydrazide to 400 ml of water containing 23.2 gm of N-methyl S-methyl isothiourea hydroiodo salt and 100 ml of 1N NaOH. Stir the reaction at room temperature for 72 hours. Isolate the isonicotinic acid 2-(methylamidino)hydrazide.

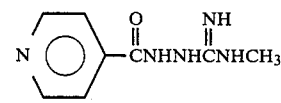

(b) Dissolve the isonicotinic acid 2-(methylamidino) hydrazide into 200 ml of N,N-dimethylformamide. Heat the system to reflux for 18 hours. Cool the system and remove the solvent by stripping. Separate the 3-(4'-pyridinyl)-5-N-methylamino-1,2,4-triazole and the 4- methyl-5-amino-3-(4'-pyridinyl)-1,2,4-triazole by chromatography using silica gel.

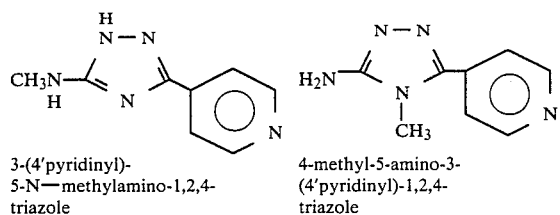

3-(4'pyridinyl)-
5-N—methylamino-1,2,4-
triazole 4-methyl-5-amino-3-
(4'pyridinyl)-1,2,4-
triazole

EXAMPLE 16

Preparation of
3-amino-1-methyl-5-(4'-pyridinyl)-1,2,4-triazole

Add 4.8 gm of sodium hydride (50% solution in mineral oil) to 100 ml of toluene containing 16.1 gm of 3-amino-5-(4'-pyridinyl)-1,2,4-triazole. Heat the system and add 14.2 gm of methyliodide. Stir the system at room temperature for 16 hours. Filter the solution and remove the solvent by stripping. Isolate the 3-amino-1-methyl-5-(4'-pyridinyl)-1,2,4-triazole by chromatography on silica gel.

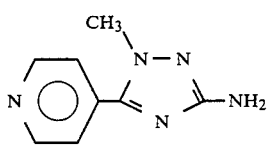

EXAMPLE 17

Preparation of
3,5-dimethyl-2-(4'-pyridinyl)-1,2,4-triazolo[1,5-a]pyrimidin-7(3H)one and
3,7-dimethyl-2-(4'-pyridinyl)-1,2,4-triazolo[1,5-a]pyrimidin-5(3H)one

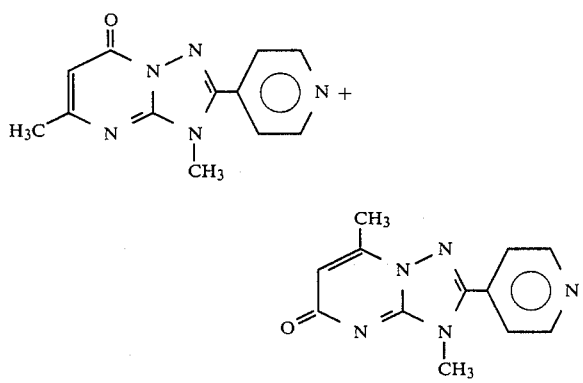

Add 17.5 gm of 5-amino-4-methyl-3-(4'-pyridinyl)-1,2,4-triazole to 50 ml of ethyl acetoacetate in 500 ml of glacial acetic acid. Heat the system in an oil bath at reflux until the reaction is complete (18 hours) as determined by thin layer chromatography on silica gel. Stop the reaction and remove the solvent by stripping. Separate the 3,5-dimethyl-2-(4'-pyridinyl)-1,2,4-triazolo[1,5-a]pyrimidin-7(3H)-one and 3,5 dimethyl-2-(4-pyridinyl)-1,2,4-triazolo[1,5-a]pyrimidin-5(3H)-one by chromatography.

EXAMPLE 18

Preparation of
4,5-dimethyl-2-(4'-pyridinyl)-1,2,4-triazolo[1,5-a]pyrimidin-7(4H)-one and
4,7-dimethyl-2-(4'-pyridinyl)-1,2,4-triazolo[1,5-a]pyrimidin-5(4H)-one

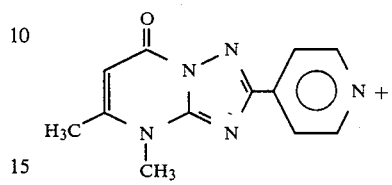

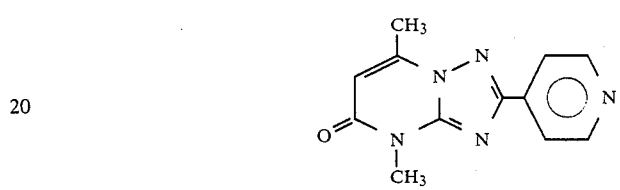

Add 26.25 gm of 5-N-methylamino-3-(4'-pyridinyl)-1,2,4-triazole to 500 ml acetic acid containing 58.5 gm of ethyl acetoacetate. Heat the system in an oil bath at reflux until the reaction is complete (18 hours) as determined by thin layer chromatography on silica gel. Stop the reaction and remove the solvent by stripping. Separate the 4,5-dimethyl-2-(4'-pyridinyl)-1,2,4-triazolo[1,5-a]pyrimidin-7(4H)-one and 4,7-dimethyl-2-(4'-pyridinyl)-1,2,4-triazolo[1,5-a]pyrimidin-5(4H)-one by chromatography.

EXAMPLE 19

Preparation of
1,5-dimethyl-2-(4'pyridinyl)-1,2,4-triazolo[1,5-a]pyrimidin-5(1H)-one

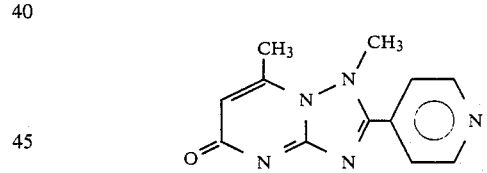

Add 17.5 gm of 3-amino-1-methyl-5-pyridinyl-1,2,4-triazole to 50 ml of ethyl acetoacetate. Heat the system in an oil bath a 160°–180° C. until the reaction is complete (½ hour) as determined by thin layer chromatography on silica gel. Stop the reaction and remove the solvent by stripping. Isolate 1,5-dimethyl-2-(4'-pyridinyl)-1,2,4-triazolo[1,5-a]pyrimidin-7(1H)-one.

Similarly by following the same procedures as outlined in the above Examples and employing the appropriate reagents, the following compounds of this invention may be prepared:

4-methyl-2-(4'pyridinyl)-1,2,4-triazolo[1,5-a]pyrimidin-7-(4H)-one;
6-chloro-4-ethyl-2-(2'-hydroxy-4'-pyridinyl)-1,2,4-triazolo[1,5-a]pyrimidin-7(4H)-one;
6-methyl-4-n-propyl-(2'-chloro-3'-methyl-4'-pyridinyl)-1,2,4-triazolo[1,5-a]pyrimidin-7(4H)-one;
6-methyl-4-methyl-2-(4'-pyridinyl)-1,2,4-triazolo[1,5-a]pyrimidin-7(4H)one;
6-amino-4-methyl-2-(3'-pyridinyl)-1,2,4-triazolo[1,5-a]pyrimidin-7(4H)-one;

6-N-acetylamino-4-isopropyl-2-(2'-pyridinyl)-1,2,4-triazolo[1,5-a]pyrimidin-7(4H)-one;
4-methyl-2-(4'-pyridinyl)-1,2,4-triazolo-[1,5-a]pyrimidin-7(4H)-one;
5,6-diamino-4-methyl-1,2,4-triazolo[1,5-a]pyrimidin-7(4H)-one;
5-N-acetylamino-4-methyl-1,2,4-triazolo[1,5-a]pyrimidin-7(4H)-one;
4-methyl-2-(4'-pyridinyl)-1,2,4-triazolo[1,5-a]pyrimidin-5(4H)-one;
6-chloro-4-ethyl-2-(2'-hydroxy-4'-pyridinyl)-1,2,4-triazolo[1,5-a]-pyrimidin-5(4H)-one;
6-methyl-4-n-propyl-2-(2'-chloro-3'-methyl-4'-pyridinyl)-1,2,4-triazolo[1,5-a]pyrimidin-5(4H)-one;
6-amino-4-methyl-2-(3'-pyridinyl)-1,2,4-triazolo[1,5-a]pyrimidin-5(4H)-one;
6-N-acetylamino-4-isopropyl-2-(2'-pyridinyl)-1,2,4-triazolo[1,5-a]pyrimidin-5-(4H)-one;
4-methyl-2-(4'-pyridinyl)-1,2,4-triazolo[1,5-a]pyrimidin-5(4H)-one-6-carboxamide;
6,7-diamino-4-methyl-1,2,4-triazolo[1,5-a]pyrimidin-5(4H)-one;
7-N-acetylamino-4-methyl-1,2,4-triazolo[1,5-a]pyrimidin-5(4H)-one;
3-methyl-2-(4'-pyridinyl)-1,2,4-triazolo[1,5-a]pyrimidin-7(3H)-one;
6-chloro-3-ethyl-2-(2'-hydroxy-4'-pyridinyl)-1,2,4-triazolo[1,5-a]pyrimidin-7(3H)-one;
6-methyl-3-n-propyl-2-(2'-chloro-3'-methyl-4'-pyridinyl)-1,2,4-triazolo[1,5-a]pyrimidin-7(3H)-one;
6-amino-3-methyl-2-(3'-pyridinyl)-1,2,4-triazolo[1,5-a]pyrimidin-7(3H)-one;
6-N-acetylamino-3-isopropyl-2-(2'-pyridinyl)-1,2,4-triazolo[1,5-a]pyrimidin-7(3H)-one;
3-methyl-2-(4'-pyridinyl)-1,2,4-triazolo[1,5-a]pyrimidin-7(3H)-one-6-carboxamide;
5,6-diamino-3-methyl-1,2,4-triazolo[1,5-a]pyrimidin-7(3H)-one;
5-N-acetylamino-3-methyl-1,2,4-triazolo[1,5-a]pyrimidin-7(3H)-one;
3-methyl-2-(4'-pyridinyl)-1,2,4-triazolo[1,5-a]pyrimidin-5(3H)-one;
6-chloro-3-ethyl-2-(2'-hydroxy-4'-pyridinyl)-1,2,4-triazolo[1,5-a]pyrimidin-5(3H)-one;
6-methyl-3-n-propyl-2-(2'-chloro-3'-methyl-4'-pyridinyl)-1,2,4-triazolo[1,5-a]pyrimidin-5(3H)-one;
6-amino-3-methyl-2-(3'-pyridinyl)-1,2,4-triazolo[1,5-a]pyrimidin-5(3H)-one;
6-N-acetylamino-3-isopropyl-2-(2'-pyridinyl)-1,2,4-triazolo[1,5-a]pyrimidin-5(3H)-one;
3-methyl-2-(4'-pyridinyl)-1,2,4-trizolo[1,5-a]pyrimidin-5(3H)-one;
6,7-diamino-3-methyl-1,2,4-triazolo[1,5-a]pyrimidin-5(3H)-one;
7-N-acetylamino-3-methyl-1,2,4-triazolo[1,5-a]pyrimidin-5(3H)-one;
1-methyl-2-(4'-pyridinyl)-1,2,4-triazolo[1,5-a]pyrimidin-7(1H)-one;
6-chloro-1-ethyl-2-(2'-hydroxy-4'-pyridinyl)-1,2,4-triazolo[1,5-a]pyrimidin-7(1H)-one;
6-methyl-1-n-propyl-2-(2'-chloro-3'-methyl-4'-pyridinyl)-1,2,4-triazolo[1,5-a]pyrimidin-7(1H)-one;
6-amino-1-methyl-2-(3'-pyridinyl)-1,2,4-triazolo[1,5-a]pyrimidin-7(1H)-one;
6-N-acetylamino-1-isopropyl-2-(2'-pyridinyl)-1,2,4-triazolo[1,5-a]pyrimidin-7(1H)-one;
1-methyl-2-(4'-pyridinyl)-1,2,4-triazolo[1,5-a]pyrimidin-7(1H)-one;
5,6-diamino-1-methyl-1,2,4-triazolo[1,5-a]pyrimidin-7(1H)-one;
5-N-acetylamino-1-methyl-1,2,4-triazolo[1,5-a]pyrimidin-7(1H)-one;
1-methyl-2-(4'-pyridinyl)-1,2,4-triazolo[1,5-a]pyrimidin-5(1H)-one;
6-chloro-1-ethyl-2-(2'-hydroxy-4'-pyridinyl)-1,2,4-triazolo[1,5-a]pyrimidin-5(1H)-one;
6-methyl-1-n-propyl-2-(2'-chloro-3'-methyl-4'-pyridinyl)-1,2,4-triazolo[1,5-a]pyrimidin-5(1H)-one;
6-amino-1-methyl-2-(3'-pyridinyl)-1,2,4-triazolo[1,5-a]pyrimidin-5(1H)-one;
6-N-acetylamino-1-isopropyl-2-(2'-pyridinyl)-1,2,4-triazolo[1,5-a]pyrimidin-5(1H)-one;
1-methyl-2-(4'-pyridinyl)-1,2,4-triazolo-[1,5-a]pyrimidin-5(1H)-one-6-carboxamide;
6,7-diamino-1-methyl-2-(4'-pyridinyl)-1,2,4-triazolo[1,5-a]pyrimidin-5(1H)-one; and
7-N-acetylamino-1-methyl-2-(4'-pyridinyl)-1,2,4-triazolo[1,5-a]pyrimidin-5(1H)-one.

EXAMPLE 20

Preparation of 4,6,6-trimethyl-2-(4'-pyridinyl)-1,2,4-triazolo[1,5-a]pyrimidin-5,7-(4H,6H)-dione

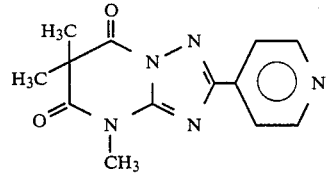

Add 26.25 gm of 5-N-methylamino-3-(4'-pyridinyl)-1,2,4-triazole to 500 ml of ethanol containing 83 gm of diethyl 2,2-dimethylmalonate and 20.2 gm of sodium ethoxide. Heat the system in an oil bath at reflux until the reaction is complete (6–10 hours) as determined by thin layer chromatography on silica gel. Stop the reaction and neutralize the systrem with acetic acid. Filter and remove the solvent by stripping. Isolate 4,6,6-trimethyl-3-(4'-pyridinyl)-1,2,4-triazolo[1,5-a]pyrimidin-5,7-(4H,6H)-dione.

EXAMPLE 21

Preparation of 3,6,6-trimethyl-2-(4'-pyridinyl)-1,2,4-triazolo[1,5-a]pyrimidin-5,7-(3H,6H)-dione

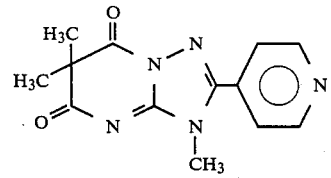

Add 17.5 gm of 5-amino-4-methyl-3-(4'-pyridinyl)-1,2,4-triazole to 500 ml of ethanol containing 56 gm of diethyl 2,2-dimethylmalonate and 13 gm of sodium ethoxide. Heat the system in an oil bath at reflux until the reaction is complete (6–10 hours) as determined by thin layer chromatography on silica gel. Stop the reaction and neutralize the system with acetic acid. Filter and remove the solvent by stripping. Isolate 3,6,6- trimethyl-2-(4'-pyridinyl)-1,2,4-triazolo[1,5-a]pyrimidin-5,7-(3H,6H)-dione.

EXAMPLE 22

Preparation of 1,6,6-trimethyl-2-(4'-pyridinyl)-1,2,4-triazolo[1,5-a]pyrimidin-5,7-(1H,6H)-dione

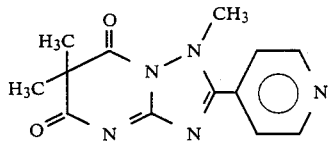

Add 17.5 gm of 3-amino-1-methyl-5-(4'-pyridinyl)-1,2,4-triazole to 500 ml of ethanol containing 56 gm of diethyl 2,2-dimethylmalonate and 13 gm of sodium ethoxide. Heat the system in an oil bath at reflux until the reaction is complete (6–10 hours) as determined by thin layer chromatography on silica gel. Stop the reaction and neutralize the system with acetic acid. Filter and remove the solvent by stripping. Isolate 1,6,6-trimethyl-2-(4'-pyridinyl)-1,2,4-triazolo[1,5-a]pyrimidin-5,7-(1H,6H)-dione.

EXAMPLE 23

Preparation of 6,6-dimethyl-2-(4'-pyridinyl)-1,2,4-triazolo[1,5-a]pyrimidin-5,7-(4H,6H)-dione

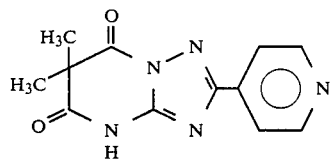

Add 56 gm of diethyl malonate to 500 ml of ethanol containing 14.9 gm of 5-amino-3-(4'-pyridinyl)-1,2,4-triazole and 13 gm of sodium ethoxide. Heat the system in an oil bath at reflux until the reaction is complete (6–10 hours) as determined by thin layer chromatography on silica gel. Stop the reaction and neutralize the system with acetic acid. Filter and remove the solvent by stripping. Isolate the title compound.

The 6,6-dimethyl-2-(4'-pyridinyl)-1,2,4-trazole[1,5-a]pyrimidin-5,7-(4H,6H)-dione is tautomeric with the 5-hydroxy as shown below.

Throughout this disclosure the term 1,2,4-triazolo[1,5-a]pyrimidin-5,7-(4H,6H)-dione shall be taken to mean any of the above tautomers.

Similarly, by following the same procedures as outlined in the Examples above and employing the appropriate reagents, the following compounds of this invention may be prepared:

6,6-diethyl-4-methyl-2-(4'-pyridinyl)-1,2,4-triazolo[1,5-a]pyrimidin-5,7(4H,6H)-dione;
4,6-diethyl-6-methyl-2-(4'-pyridinyl)-1,2,4-triazolo[1,5-a]pyrimidin-5,7(4H,6H)-dione;
3,6,6-triethyl-2-(4'-pyridinyl)-1,2,4-triazolo[1,5-a]pyrimidin-5,7(3H,6H)-dione;
1,6,6-triethyl-2-(4'-pyridinyl)-1,2,4-triazolo[1,5-a]pyrimidin-5,7(1H,6H)-dione; and
6,6-diethyl-2-(4'-pyridinyl)-1,2,4-triazolo[1,5-a]pyrimidin-5,7(4H,6H)-dione.

The following formuations exemplify some of the dosage forms in which the compounds of this invention may be employed. In each, the active ingredient is designated by the term "Drug" which is meant to indicate one of the following compounds:

5,7-dimethyl-2-(4'-pyridinyl)-1,2,4-triazolo[1,5-a]pyrimidine;
5,7-dimethyl-2-(3'-methyl-4'-pyridinyl)-1,2,4-triazolo[1,5-a]pyrimidine; and
Ethyl 7-hydroxy-2-(4'-pyridinyl)-1,2,4-triazolo[1,5-a]pyrimidine-6-carboxylate.

It is contemplated, however, that each of these exemplar compounds may be replaced by equally effective quantities of other compounds within the scope of Formula A to C. All temperatures are in degrees Celsius.

EXAMPLE 24

Capsules

| No. | Ingredient | mg/capsule | mg/capsule |
|-----|------------|------------|------------|
| 1. | Drug | 250 | 500 |
| 2. | Lactose USP | 100 | 50 |
| 3. | Corn Starch, Food Grade | 50 | 43.5 |
| 4. | Microcrystalline Cellulose | 95 | 50 |
| 5. | Magnesium Stearate NF | 5 | 6.5 |
|  | Total | 500 | 650 |

Method of Manufacture

Mix Item Nos. 1, 2, 3 and 4 in a suitable mixer for 10–15 minutes. Add Item No. 5 and mix for 1–3 minutes. Fill the mixture into suitable two-piece hard gelatin capsules using suitable encapsuling machine.

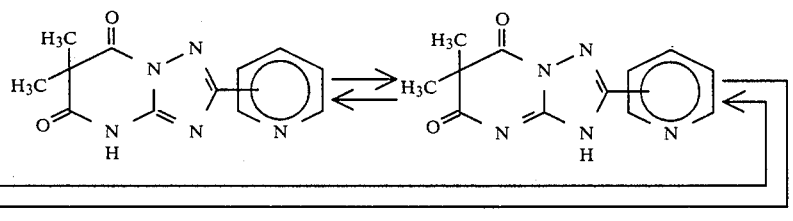

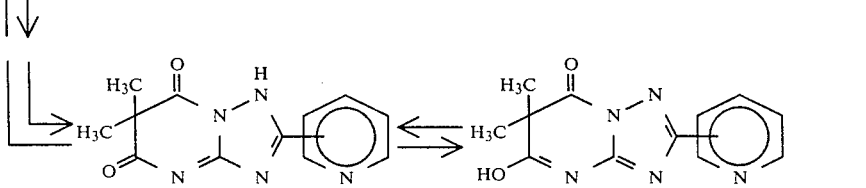

EXAMPLE 25

Tablets

| No. | Ingredient | mg/tablet | mg/tablet |
|---|---|---|---|
| 1. | Drug | 250 | 500 |
| 2. | Lactose USP | 57 | 114 |
| 3. | Corn Starch, Food Grade, as a 10% paste in Purified Water | 20 | 40 |
| 4. | Corn Stach, Food Grade | 18 | 39 |
| 5. | Magnesium Stearate NF | 5 | 7 |
|   | Total | 350 | 700 |

Method of Manufacture

Mix Item Nos. 1 and 2 in a suitable mixer for 10–15 minutes. Granulate the mixture with Item No. 3. Pass the wet granulation through a coarse screen (e.g., ¼″) if needed, and dry the wet granules. Mill the dried granules. Combine Item No. 4 and the dried granules and mix for 10–15 minutes. Add Item No. 5 and mix for 1–3 minutes. Compress the mixture to appropriate size and weight on a suitable tablet machine.

EXAMPLE 26

Parenteral Dosage Forms (a) Injection (Per vial)

|   | mg/vial |
|---|---|
| Drug Sterile powder | 500 |

Add sterile water for injection or bacteriostatic water for injection for reconstitution.

(b) Injectable Solution of drug

| Ingredient | mg/ml |
|---|---|
| Drug | 20 |
| Methylparaben | 0.2 |
| Propylparaben | 1.6 |
| Sodium Bisulfite | 3.2 |
| Disodium Edetate | 0.1 |
| Water for Injection q.s. ad | 1.0 ml |

Method of Manufacture

1. Dissolve parabens in a portion (85% of the final volume) of the water for injection at 65°–70° C.
2. Cool to 25°–35° C. Charge and dissolve the sodium bisulfite and disodium edetate.
3. Charge and dissolve Drug.
4. Bring the solution to final volume by adding water for injection.
5. Filter the solution through 0.22 membrane and fill into appropriate contains.
6. Terminally sterilize the units by autoclaving.

I claim:

1. A compound selected from the group consisting of

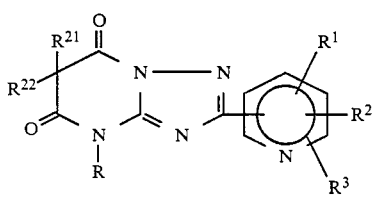

-continued

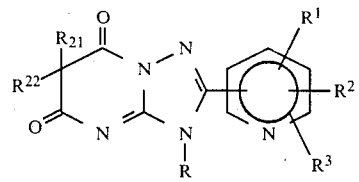

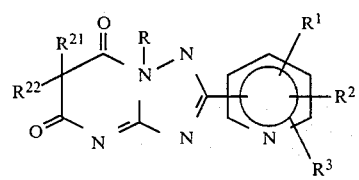

wherein
  R is hydrogen, lower alkyl or lower aralkyl;
  $R^1, R^2$ and $R^3$ are independently selected from hydrogen, halogen, hydroxy, lower alkoxy, lower alkyl and amino;
  $R^{21}$ and $R^{22}$ are independently lower alkyl;
and the pharmaceutically acceptable salts thereof.

2. A compound selected from the group consisting of 5,7-dimethyl-2-(4′-pyridinyl)-1,2,4-triazolo[1,5-a]pyrimidine; 7-N,N-diethylamino-5-methyl-2-(4′-pyridinyl)-1,2,4-triazolo[1,5-a]pyrimidine; 5,7-dimethyl-2-(6′-hydroxy-3′-pyridinyl)-1,2,4-triazolo[1,5-a]pyrimidine; 5,7-dimethyl-2-(2′-methyl-4′pyridinyl)-1,2,4-triazolo[1,5-a]pyrimidine and 5,7-dimethyl-2-(2′-hydroxy-4′-pyridinyl)-1,2,4-triazolo[1,5-a]pyrimidine.

3. A compound of claim 2 which is 5,7-dimethyl-2-(4′-pyridinyl)-1,2,4-triazolo[1,5-a]pyrimidine.

4. A compound of claim 2 which is N,N-diethylamino-5-methyl-2-(4′-pyridinyl)-1,2,4-triazolo[1,5-a]pyrimidine.

5. A compound of claim 2 which is 5,7-dimethyl-2-(6′-hydroxy-3′-pyridinyl)-1,2,4-triazolo[1,5-a]pyrimidine.

6. A compound of claim 2 which is 5,7-dimethyl-2-(2′-methyl-4′-pyridinyl)-1,2,4-triazolo[1,5-a]pyrimidine.

7. A compound of claim 2 which is 5,7-dimethyl-2-(2′-hydroxy-4′-pyridinyl)-1,2,4-triazolo[1,5-a]pyrimidine.

8. A compound represented by the formula

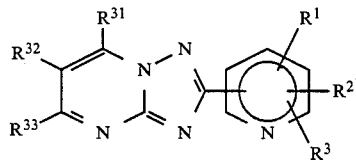

wherein
  $R^1$, $R^2$ and $R^3$ are independently selected from hydrogen, hydroxy and lower alkyl, and wherein the pyridinyl group is selected from 6′-hydroxy-3′-pyridinyl, 2′-methyl-4′-pyridinyl and 2′-hydroxy-4′-pyridinyl and
  $R^{31}, R^{32}$ and $R^{33}$ are independently selected from hydrogen, lower alkyl, hydroxy, cyano, $-NR^4R^5$ wherein $R^4$ is hydrogen, lower alkyl, or

wherein R⁶ is lower alkyl, and R⁵ is hydrogen, lower alkyl, or together with R⁴ is joined to form a ring containing 4 to 6 carbon atoms,

wherein R⁷ is hydroxy, lower alkoxy, or —NR⁸R⁹ wherein R⁸ and R⁹ are independently selected from hydrogen or lower alkyl; or

wherein M is sulfur or NH;
and the pharmaceutically acceptable salts thereof.

9. A compound represented by the formula

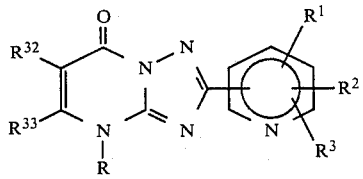

wherein
R is hydrogen, lower alkyl or lower aralkyl;
R¹, R² and R³ are independently selected from hydrogen, halogen, hydroxy, lower alkoxy, lower alkyl and amino;
R³² and R³³ are independently selected from hydrogen, lower alkyl, hydroxy, cyano, —NR⁴R⁵ wherein R⁴ is hydrogen, lower alkyl, or

wherein R⁶ is lower alkyl, and R⁵ is hydrogen, lower alkyl, or together with R⁴ is joined to form a ring containing 4 to 6 carbon atoms,

wherein R⁷ is hydroxy, lower alkoxy, or —NR⁸R⁹ wherein R⁸ and R⁹ are independently selected from hydrogen or lower alkyl; or

wherein M is sulfur or NH;
and the pharmaceutically acceptable salts thereof.

10. A compound of claim 9 wherein the pyridinyl group is R'-pyridinyl.

11. A compound of claim 10 wherein R and R³³ are methyl and R³² is hydrogen; ie 4,5-dimethyl-2-(4'-pyridinyl)-1,2,4-triazolo[1,5-a]pyrimidin-7-(4H)-one.

12. A compound represented by the formula

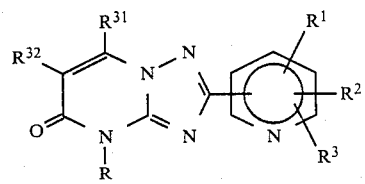

wherein
R is hydrogen, lower alkyl or lower aralkyl;
R¹, R² and R³ are independently selected from hydrogen, halogen, hydroxy, lower alkoxy, lower alkyl and amino;
R³¹ and R³² are independently selected from hydrogen, lower alkyl, hydroxy, cyano, —NR⁴R⁵ wherein R⁴ is hydrogen, lower alkyl, or

wherein R⁶ is lower alkyl, and R⁵ is hydrogen, lower alkyl, or together with R⁴ is joined to form a ring containing 4 to 6 carbon atoms,

wherein R⁷ is hydroxy, lower alkoxy, or —NR⁸R⁹ wherein R⁸ and R⁹ are independently selected from hydrogen or lower alkyl;

wherein M is sulfur or NH;
and the pharmaceutically acceptable salts thereof.

13. A compound represented by the formula

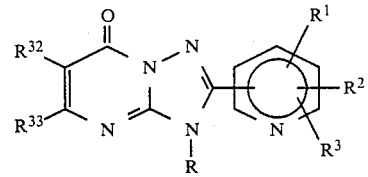

wherein
R is hydrogen, lower alkyl or lower aralkyl;
R¹, R² and R³ are independently selected from hydrogen, halogen, hydroxy, lower alkoxy, lower alkyl and amino;
R³² and R³³ are independently selected from hydrogen, lower alkyl, hydroxy, cyano, —NR⁴R⁵ wherein R⁴ is hydrogen, lower alkyl, or

wherein R⁶ is lower alkyl, and R⁵ is hydrogen, lower alkyl, or together with R⁴ is joined to form a ring containing 4 to 6 carbon atoms, wherein $R^7$ is hydroxy, lower alkoxy, or $-NR^8R^9$ wherein $R^8$ and $R^9$ are independently selected from hydrogen or lower alkyl;

$$-\overset{M}{\underset{\|}{C}}NH_2$$

wherein M is sulfur or NH;
and the pharmaceutically acceptable salts thereof.

14. A compound of claim 13 wherein the pyridinyl group is 4'-pyridinyl.

15. A compound of claim 14 wherein R and $R^{33}$ are methyl and $R^{32}$ is hydrogen; ie 3,5-dimethyl-2-(4'-pyridinyl)-1,2,4-triazolo[1,5-a]pyrimidin-7(3H)-one.

16. A compound represented by the formula wherein
R is hydrogen, lower alkyl or lower aralkyl;
$R^1$, $R^2$ and $R^3$ are independently selected from hydrogen, halogen, hydroxy, lower alkoxy, lower alkyl and amino;
$R^{32}$ and $R^{33}$ are independently selected from hydrogen, lower alkyl, hydroxy, cyano, $-NR^4R^5$ wherein $R^4$ is hydrogen, lower alkyl, or $$-\overset{O}{\underset{\|}{C}}R^6$$

wherein $R^6$ is lower alkyl, and $R^5$ is hydrogen, lower alkyl, or together with $R^4$ is joined to form a ring containing 4 to 6 carbon atoms, $$-\overset{O}{\underset{\|}{C}}R^7$$

wherein $R^7$ is hydrogen, lower alkoxy, or $-NR^8R^9$
wherein $R^8$ and $R^9$ are independently selected from hydrogen or lower alkyl;

$$-\overset{M}{\underset{\|}{C}}NH_2$$

wherein M is sulfur or NH; and the pharmaceutically acceptable salts thereof.

17. A compound of claim 16 wherein the pyridinyl group is 4'-pyridinyl.

18. A compound of claim 17 wherein R and $R^{33}$ are methyl and $R^{32}$ is hydrogen; ie 1,5-dimethyl-2-(4-pyridinyl)-1,2,4-triazolo[1,5-a]pyrimidin-7(1H)-one.

19. A compound represented by the formula wherein
R is hydrogen, lower alkyl or lower aralkyl;
$R^1$, $R^2$ and $R^3$ are independently selected from hydrogen, halogen, hydroxy, lower alkoxy, lower alkyl and amino;
$R^{21}$ and $R^{22}$ are independently selected from hydrogen or lower alkyl;
and the pharmaceutically acceptable salts thereof.

20. A method for increasing cardiac contractility in a patient requiring such treatment which comprises administering an amount effective in increasing cardiac contractility of a compound of the formula selected from the group consisting of wherein
W and X together with the carbon and nitrogen of the triazolo ring are joined to form a heterocyclic ring selected from the group consisting of Y and Z together with the carbon and nitrogen of the triazolo ring are joined to form a heterocyclic ring selected from the group consisting of

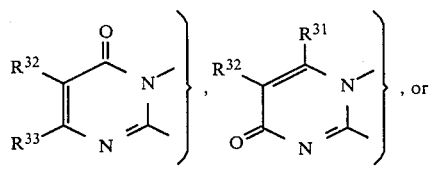

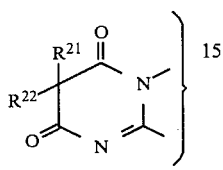

, or

R is hydrogen, lower alkyl or lower aralkyl;

$R^1$, $R^2$ and $R^3$ are independently selected from hydrogen, halogen, hydroxy, lower alkoxy, lower alkyl and amino;

$R^{31}$, $R^{32}$ and $R^{33}$ are independently selected from hydrogen, lower alkyl, hydroxy, cyano, —$NR^4R^5$ wherein $R^4$ is hydrogen, lower alkyl, or

wherein $R^6$ is lower alkyl, and $R^5$ is hydrogen, lower alkyl, or together with $R^4$ is joined to form a ring containing 4 to 6 carbon atoms,

wherein $R^7$ is hydroxy, lower alkoxy, or —$NR^8R^9$ wherein $R^8$ and $R^9$ are independently selected from hydrogen or lower alkyl;

wherein M is sulfur or NH; $R^{21}$ and $R^{22}$ are independently selected from hydrogen or lower alkyl; and the pharmaceutically acceptable salts thereof.

21. The method of claim 20 wherein said compound is administered orally.

22. The method of claim 20 wherein said compound is administered parenterally.

23. A pharmaceutical composition comprising a pharmaceutically acceptable carrier and an amount effective in increasing cardiac contractility of a compound of the formula selected from the group consisting of

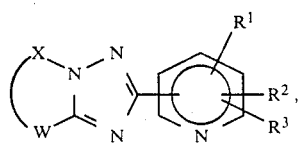

-continued

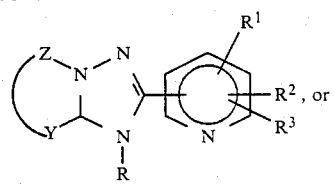

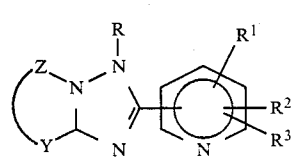

wherein

W and X together with the carbon and nitrogen of the triazolo ring are joined to form a heterocyclic ring selected from the group consisting of

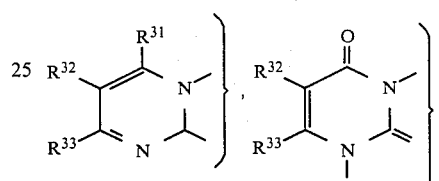

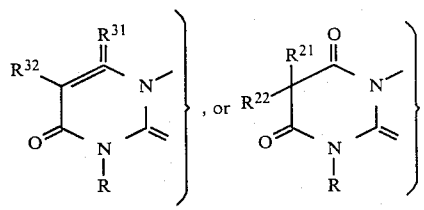

Y and Z together with the carbon and nitrogen of the triazolo ring are joined to form a heterocyclic ring selected from the group consisting of

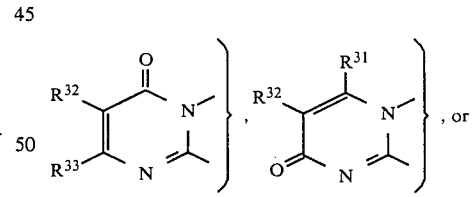

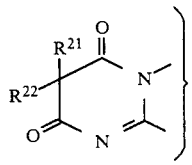

R is hydrogen, lower alkyl or lower aralkyl;

$R^1$, $R^2$ and $R^3$ are independently selected from hydrogen, halogen, hydroxy, lower alkoxy, lower alkyl and amino;

$R^{31}$, $R^{32}$ and $R^{33}$ are independently selected from hydrogen, lower alkyl, hydroxy, cyano, —$NR^4R^5$ wherein $R^4$ is hydrogen, lower alkyl, or

wherein $R^6$ is lower alkyl, and $R^5$ is hydrogen, lower alkyl, or together with $R^4$ is joined to form a ring containing 4 to 6 carbon atoms,

wherein $R^7$ is hydroxy, lower alkoxy, or $-NR^8R^9$ wherein $R^8$ and $R^9$ are independently selected from hydrogen or lower alkyl;

wherein M is sulfur or NH; $R^{21}$ and $R^{22}$ are independently selected from hydrogen or lower alky; and the pharmaceutically acceptable salts thereof.

24. The composition of claim 23 wherein said composition is adapted for oral administration.

25. The composition of claim 23 wherein said composition is adapted for parenteral administration.

26. A compound of claim 12 wherein R and $R^{31}$ are methyl, the pyridinyl group is 4'-pyridinyl and $R^{32}$ is hydrogen; i.e. 4,7-dimethyl-2-(4'-pyridinyl)-1,2,4-triazolo (1,5-a)pyrimidin-5(4H)-one.

* * * * *